United States Patent
Ahmed et al.

(10) Patent No.: US 11,337,635 B2
(45) Date of Patent: May 24, 2022

(54) AUTOMATIC CARDIOVASCULAR DISEASE DIAGNOSTIC SYSTEM AND METHOD

(71) Applicant: KING ABDULLAH UNIVERSITY OF SCIENCE AND TECHNOLOGY, Thuwal (SA)

(72) Inventors: Sajid Ahmed, Thuwal (SA); Mohamed-Slim Alouini, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 17/427,162

(22) PCT Filed: Mar. 8, 2021

(86) PCT No.: PCT/IB2021/051915
§ 371 (c)(1),
(2) Date: Jul. 30, 2021

(87) PCT Pub. No.: WO2021/181247
PCT Pub. Date: Sep. 16, 2021

(65) Prior Publication Data
US 2022/0039727 A1 Feb. 10, 2022

Related U.S. Application Data

(60) Provisional application No. 63/009,224, filed on Apr. 13, 2020, provisional application No. 62/987,518, filed on Mar. 10, 2020.

(51) Int. Cl.
*A61B 5/00* (2006.01)
*A61B 5/352* (2021.01)
*A61B 5/355* (2021.01)
*A61B 5/353* (2021.01)

(52) U.S. Cl.
CPC .............. *A61B 5/352* (2021.01); *A61B 5/353* (2021.01); *A61B 5/355* (2021.01); *A61B 5/7203* (2013.01)

(58) Field of Classification Search
CPC ........ A61B 5/352; A61B 5/7235–7264; A61B 5/346–366; A61B 5/7282; A61B 5/353; A61B 5/355; A61B 5/7203
See application file for complete search history.

(56) References Cited

PUBLICATIONS

Adeluyi, O., et al., "R-Reader: A Lightweight Algorithm for Rapid Detection of ECG Signal R-peaks," 2011 2nd International Conference on Engineering and Industries (ICEI), Seogwipo, South Korea, Nov. 29-Dec. 1, 2011, pp. 1-5, IEEE.

(Continued)

*Primary Examiner* — Scott M. Getzow
(74) *Attorney, Agent, or Firm* — Patent Portfolio Builders PLLC

(57) ABSTRACT

A method for automatically and independently associating a cardiovascular disease with an electrocardiogram, ECG, signal includes receiving the ECG signal; denoising the ECG signal using a wavelet transform; determining peaks of the denoised ECG signal by applying a combination of (1) two event-related moving averages and (2) fractional-Fourier-transform (FrFT) to the denoised ECG signal; and passing the peaks through a classifier for identifying the cardiovascular disease that corresponds to the ECG signal.

10 Claims, 20 Drawing Sheets

(56) References Cited

PUBLICATIONS

Bajaj, A., et al., "QRS Complex Detection Using Fractional Stockwell Transform and Fractional Stockwell Shannon Energy," Biomedical Signal Processing and Control, Aug. 9, 2019, vol. 54, pp. 1-12, Elsevier, Amsterdam, NL.

Chen, S.-W., et al., "A Real-Time QRS Detection Method Based on Moving-Averaging Incorporating with Wavelet Denoising," Computer Methods and Programs in Biomedicine, Jun. 1, 2006, vol. 82, No. 3, pp. 187-195, Elsevier, Amsterdam, NL.

Elgendi, M., "Fast GRS Detection with an Optimized Knowledge-Based Method: Evaluation on 11 Standard ECG Databases," PloS One, Sep. 16, 2013, vol. 8, No. 9, pp. e73557, 1-18.

Elgendi, M., "TERMA Framework for Biomedical Signal Analysis: An Economic-Inspired Approach," Biosensors, Nov. 2, 2016, vol. 6, No. 4, pp. 1-19.

Elgendi, M., et al., "A Proof-of-Concept Study: Simple and Effective Detection of P and T Waves in Arrhythmic ECG Signals," Bioengineering, Oct. 17, 2016, vol. 3, No. 26, pp. 1-14.

Elgendi, M., et al., "R Wave Detection using Coiflets Wavelets," 2009 IEEE 35th Annual Northeast Bioengineering Conference, Cambridge, MA, USA, Apr. 3-5, 2009, pp. 1-2, IEEE.

He, R., et al., "Short-Time Detection of QRS Complexes Using Dual Channels Based on U-Net and Bidirectional Long Short-Term Memory," arxiv.org, Cornell University Library, 201 Olin Library Cornell University, Ithaca, NY, 14853, Dec. 18, 2019, XP081569547.

International Search Report in corresponding/related International Application No. PCT/IB2021/051915, dated May 25, 2021.

Karthikeyan, P., et al., "ECG Signal Denoising Using Wavelet Thresholding Techniques in Human Stress Assessment," International Journal on Electrical Engineering and Informatics, Jul. 2012, vol. 4, No. 2, pp. 306-319.

Mabrouki, R., et al., "R Peak Detection in Electrocardiogram Signal Based on a Combination between Empirical Mode Decomposition and Hilbert Transform," 1st International Conference on Advanced Technologies for Signal and Image Processing (ATSIP) 2014, Sousse, Tunisia, Mar. 17-19, 2014, pp. 183-187, IEEE.

Ozaktas, H.M., et al., "Digital Computation of the Fractional Fourier Transform," IEEE Transactions on Signal Processing, Sep. 1996, vol. 44, No. 9, pp. 2141-2150, IEEE.

Revathi, J., et al., "A Survey on Analysis of ST-Segment to Diagnose Coronary Artery Disease," International Conference on Signal Processing and Communication (ICSPC'17), Jul. 28 & 29, 2017, pp. 211-216, IEEE.

Subramaniam, S.R., et al., "Motion Artifact Suppression in the ECG Signal by Successive Modifications in Frequency and Time," 2013 35th Annual International Conference of the IEEE Engineering in Medicine and Biology Society (EMBC), Osaka, Japan, Jul. 3-7, 2013, pp. 425-428, IEEE.

Vega-Martínez, G., "ECG Baseline Drift Removal Using Discrete Wavelet Transform," 2011 8th International Conference on Electrical Engineering, Computing Science and Automatic Control, Merida City, Mexico, Oct. 26-28, 2011, pp. 1-5, IEEE.

Written Opinion of the International Searching Authority in corresponding/related International Application No. PCT/IB2021/051915, dated May 25, 2021.

Yaqoob, T., et al., "Fractional Fourier Transform Based QRS Complex Detection in ECG Signal," ICASSP 2020-2020 IEEE International Conference on Acoustics, Speech and Signal Processing (ICASSP), Barcelona, Spain, May 14, 2020, pp. 931-935, IEEE.

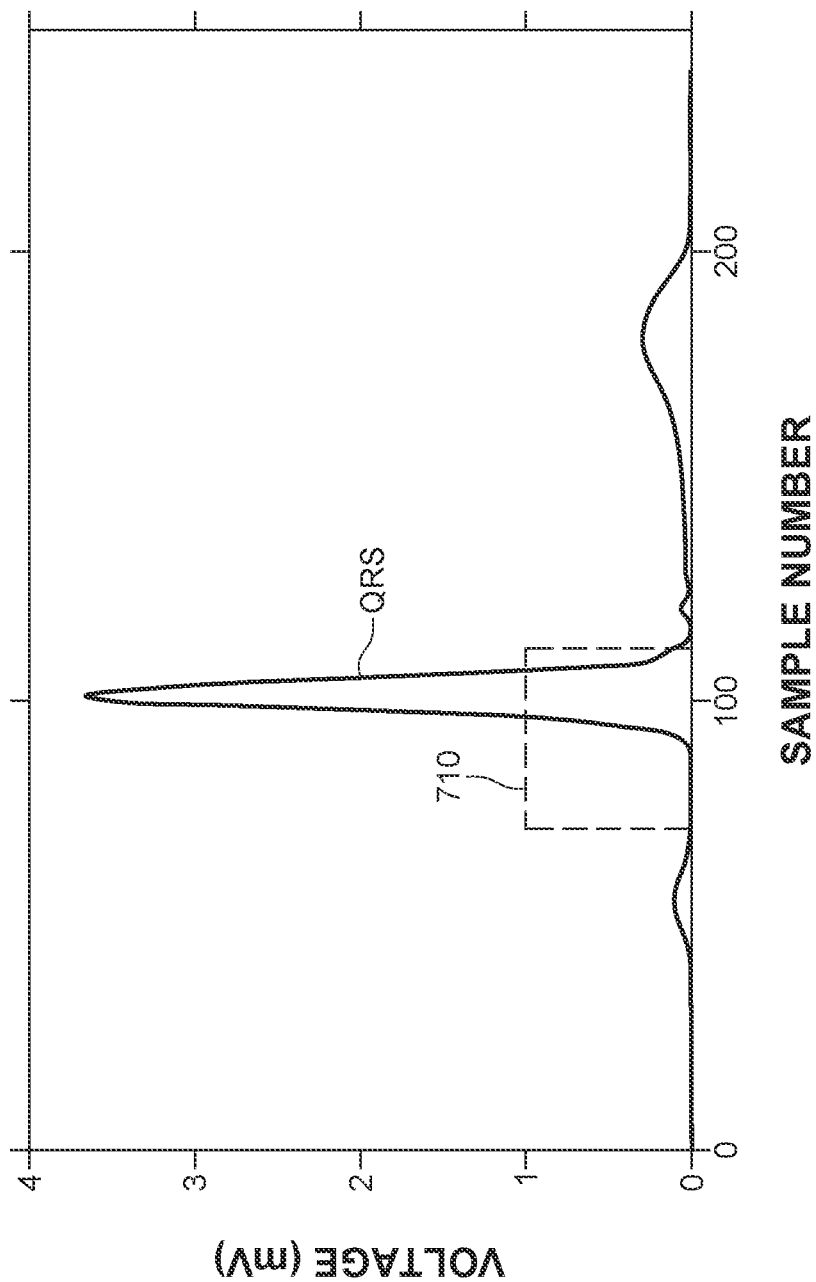

TABLE 1

| Algorithms | SE(%) | +Pr(%) | Err |
|---|---|---|---|
| Proposed Algorithm | 99.83 | 99.90 | 0.00259 |
| TERMA | 99.78 | 99.87 | 0.00298 |

FIG. 13

TABLE 2

| Algorithms | Detection of P Peaks | | Detection of T Peaks | |
|---|---|---|---|---|
| | SE(%) | +Pr(%) | SE(%) | +Pr(%) |
| Proposed Algorithm | 99.28 | 99.05 | 99.94 | 99.83 |
| TERMA | 98.05 | 97.11 | 99.86 | 99.65 |

FIG. 14A

TABLE 3

| Algorithms | Detection of P Peaks | | Detection of T Peaks | |
|---|---|---|---|---|
| | SE(%) | Err | SE(%) | Err |
| Proposed Algorithm | 75.8 | 0.40 | 67.5 | 0.51 |
| TERMA | 59.2 | 1.04 | 42.8 | 1.15 |

FIG. 14B

TABLE 4

| No of Features | Extracted Features | Overall Accuracy |
|---|---|---|
| 36 | AR+DWT | 99.6% |
| 4 | AR | 92.6% |
| 38 | AR+DWT+PR+RT | 99.6% |
| 34 | DWT+PR+RT | 83.7% |
| 6 | AR+PR+RT | 96% |
| 8 | AR+PR+RT+Age+Sex | 98.4% |
| 40 | AR+DWT+PR+RT+Age+Sex | 99.8% |

FIG. 15

TABLE 5

| Diseases | SVM | | | MLP | | |
|---|---|---|---|---|---|---|
| | Precision | Recall | f1-Score | Precision | Recall | f1-Score |
| Normal | 0.983 | 0.970 | 0.977 | 1.000 | 1.000 | 1.000 |
| LBBB | 0.971 | 0.991 | 0.981 | 0.993 | 0.999 | 0.996 |
| RBBB | 0.959 | 0.972 | 0.965 | 0.998 | 1.000 | 0.999 |
| PACE | 0.886 | 0.815 | 0.849 | 1.000 | 0.997 | 0.998 |
| PVC | 0.985 | 0.992 | 0.989 | 0.998 | 1.000 | 0.999 |
| APC | 0.971 | 0.977 | 0.974 | 1.000 | 0.992 | 0.996 |

FIG. 16

TABLE 6

| Diseases | Precision | Recall | f1-Score |
|---|---|---|---|
| AFIB | 1.000 | 0.8 | 0.889 |
| SB | 1.000 | 1.000 | 1.000 |
| SR | 0.833 | 1.000 | 0.909 |
| GSVT | 1.000 | 1.000 | 1.000 |
| Macro Average | 0.958 | 0.950 | 0.949 |
| Weighted Average | 0.958 | 0.950 | 0.949 |

FIG. 17

AUTOMATIC CARDIOVASCULAR DISEASE DIAGNOSTIC SYSTEM AND METHOD

CROSS-REFERENCE TO RELATED APPLICATIONS

This application is a U.S. National Stage Application of International Application No. PCT/IB2021/051915, filed on Mar. 8, 2021, which claims priority to U.S. Provisional Patent Application No. 62/987,518, filed on Mar. 10, 2020, entitled "AUTOMATIC CARDIOVASCULAR DISEASE DIAGNOSIS USING ECG SIGNALS," and U.S. Provisional Patent Application No. 63/009,224, filed on Apr. 13, 2020, entitled "AUTOMATIC CARDIOVASCULAR DISEASE DIAGNOSIS USING ECG SIGNALS," the disclosures of which are incorporated herein by reference in their entirety.

BACKGROUND

Technical Field

Embodiments of the subject matter disclosed herein generally relate to a system that automatically diagnosticates cardiovascular diseases based on electrocardiogram (ECG) signals, and more particularly, to a system that uses a combination of two-event related moving-averages and fractional-Fourier-transform (FrFT) to determine peaks in the ECG signals and a machine learning algorithm to automatically identify a cardiovascular disease based on the determined peaks.

DISCUSSION OF THE BACKGROUND

According to the World Health Organization (WHO), cardiovascular diseases (CVDs) are the leading cause of death globally. In recent years, various programs and policies have been implemented in increasingly diverse communities to provide tools, strategies, and other best practices to reduce the incidence of initial and recurrent cardiovascular events. To achieve this goal, the ECG has become the most commonly used bio-signal for the prompt detection of CVDs. The ECG is a graphical representation of the heart's electrical activity. It is currently used by doctors to identify various heart diseases and abnormalities.

Doctors have been using ECG signals to detect heart diseases such as arrhythmia and myocardial infarctions for over 70 years. As illustrated in FIG. 1, an ECG signal 100 includes a P wave, a QRS complex, and a T wave. An additional U wave (not shown) may also be present. Many cardiovascular diseases can be diagnosed by analyzing the variations of these waves. The traditional ECG machines are safe and inexpensive, but various factors, such as patients' body movement, movement of the electrodes placed on the body, and power line interference, may negatively impact the ECG signal. These factors may generate artifacts that may result in producing spikes in an ECG signal, which make the identification of the cardiovascular disease more difficult.

Different transforms are used for the pre-processing of the ECG signals to remove the noise and/or artifacts. For noise and artifact-free ECG signals, several algorithms are reported in the literature to detect the P, QRS complex, and T waves. These algorithms are validated over the MIT-BIH arrhythmia database [1]-[6]. In [1], a rapid-ramp effective algorithm for the detection of the R-peak is presented, which uses the slopes between adjacent signals to determine the occurrence of the R-peak. This algorithm is applied only on two records of the database and has a higher-order complexity. In [2], a combination algorithm based on an empirical-mode-decomposition (EMD) and the Hilbert transform is presented to detect the R peaks in the ECG signal. This algorithm is complicated and involves a large number of blocks for the detection of the R-peaks. In [3]-[6], algorithms based on the two event-related moving averages (TERMA) are proposed for the detection of the P, R, and T peaks. This algorithm involves different functional blocks such as filtering, enhancing, block-of-interests (BOIs) generation, and thresholding. The obtained signal is filtered with a Butterworth filter and output values are squared to enhance large values and minimize small values. After enhancement, the next step is to select the window sizes. The window sizes are selected on the basis of the QRS duration and QRS repetition interval. BOIs are generated for each peak using moving averages. Then, the width of each block is calculated. The obtained block width is compared with a threshold depending on the window size. After thresholding, the peaks are detected. For the localization of the P and T peaks, the samples before and after the detected R peaks, along with the R peak sample are all set to zero depending upon the PR interval. This algorithm gives acceptable results for the peak detection.

However, the existing algorithms are not as accurate as desired, some are complicated, which require intense computing capabilities, and some are expensive. Thus, there is a need for a new system and method that is capable to automatically detect cardiovascular diseases based on received ECG signals, and the system needs to be inexpensive and easy to use.

BRIEF SUMMARY OF THE INVENTION

According to an embodiment, there is a method for automatically and independently associating a cardiovascular disease with an electrocardiogram, ECG, signal. The method includes receiving the ECG signal; denoising the ECG signal using a wavelet transform; determining peaks of the denoised ECG signal by applying a combination of (1) two event-related moving averages and (2) fractional-Fourier-transform (FrFT) to the denoised ECG signal; and passing the peaks through a classifier for identifying the cardiovascular disease that corresponds to the ECG signal.

According to another embodiment, there is a system for automatically and independently associating a cardiovascular disease with an electrocardiogram, ECG, signal. The system includes an interface for receiving the ECG signal, and a logic circuit connected to the interface. The logic circuit is configured to denoise the ECG signal using a wavelet transform, determine peaks of the denoised ECG signal by applying a combination of (1) two event-related moving averages and (2) fractional-Fourier-transform (FrFT) to the denoised ECG signal, and pass the peaks through a classifier for identifying the cardiovascular disease that corresponds to the ECG signal.

According to yet another embodiment, there is a non-transitory computer readable medium including computer executable instructions, wherein the instructions, when executed by a computer, implement the method discussed above.

BRIEF DESCRIPTION OF THE DRAWINGS

For a more complete understanding of the present invention, reference is now made to the following descriptions taken in conjunction with the accompanying drawings, in which:

FIG. 5A illustrates the ECG signal with baseline drift and high-frequency noise while

FIG. 7 illustrates a block of interest for an ECG signal for the peak detection method;

FIG. 13 illustrates a performance comparison between the fusion method and an existing algorithm for the R peak detection;

FIG. 14A illustrates a performance comparison between the fusion method and an existing algorithm for the P and T peaks detection for a first part of the MIT-BIH database and FIG. 14B illustrates the same for a second part of the same database;

FIG. 15 illustrates the performance of the support vector machine (SVM) classifier on the MIT-BIH database;

FIG. 16 illustrates the performance comparison of the SVM and multi-layer perceptron (MLP) classifiers;

FIG. 17 illustrates the classification results of the fusion method when using the 12-lead ECG database.

DETAILED DESCRIPTION OF THE INVENTION

Figure 1:
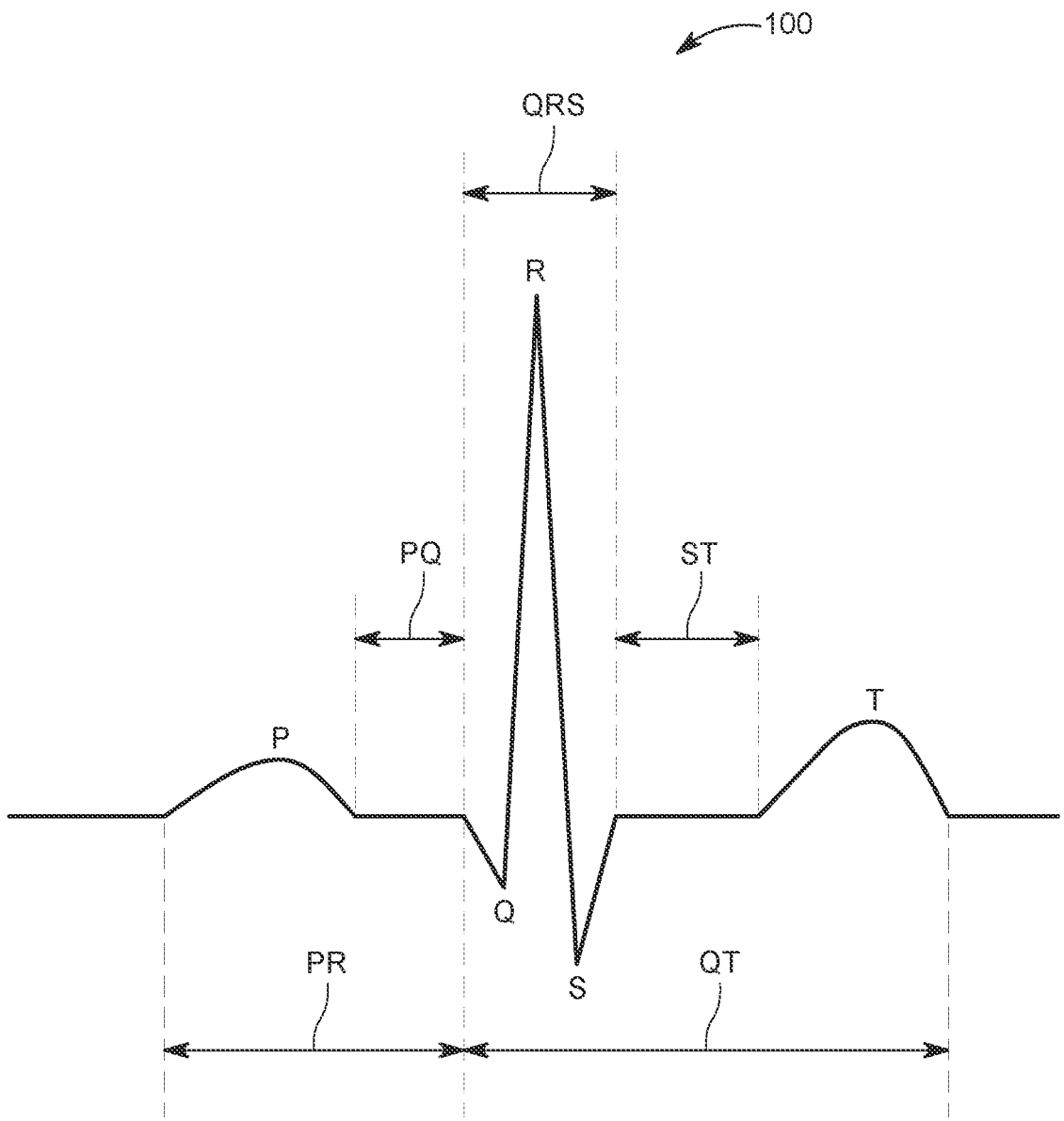
FIG. 1 is a schematic diagram of an ECG signal.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to autonomous and independent cardiovascular disease diagnostic system that based on received ECG signals, is configured to determine the various peaks of the ECG signals based on a combination of the TERMA and FrFt algorithms and then to identify the associated disease using a machine learning algorithm. However, the embodiments to be discussed next are not limited to an autonomous and independent cardiovascular disease diagnostic system, but may also be used for other diseases that are associated with other bio-signals.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a novel cardiovascular disease diagnostic system is configured to use a combination of the moving averages and time-frequency analysis to identify the peaks of the waves of the heart beat from the ECG signals, and then to classify the various detected peaks using a machine learning algorithm. Such a system 200 is shown schematically in FIG. 2 and includes a logic circuit 202, for example, a processor or integrated circuit, a memory 220 that is configured to store information (e.g., ECG signals) and/or commands, an interface 230 that can be connected to one or more sensors 232 to be attached to a person for collecting the ECG signals, a power source 240 for supplying electrical energy to the above noted components, and a communication unit 250 for transmitting and/or receiving information from an external device 270, e.g., a server, computer, smart device, cell tower, router, etc. The communication unit 250 may be a transceiver that is configured to send and receive radio frequency (RF) signals, or any other know frequency that is used for data communication.

The logic circuit 202 may include a first module 204 for pre-processing the ECG signals, for example, for removing noise from these signals. The logic circuit 202 may also include a second module 206, which is an ECG peak detection module. This module is configured to apply the TERMA and FrFT algorithms to the denoised ECG signals to estimate the peaks of the ECG signals. The logic circuit 202 may further include a cardiovascular diagnosis module 208, which is configured to receive the peaks of the ECG signals from the ECG processing module 206, and to use one or more machine learning algorithms to determine a cardiovascular disease that fits the peaks of the ECG signals. Each of these modules and their actions are discussed in detail later.

Figure 3:
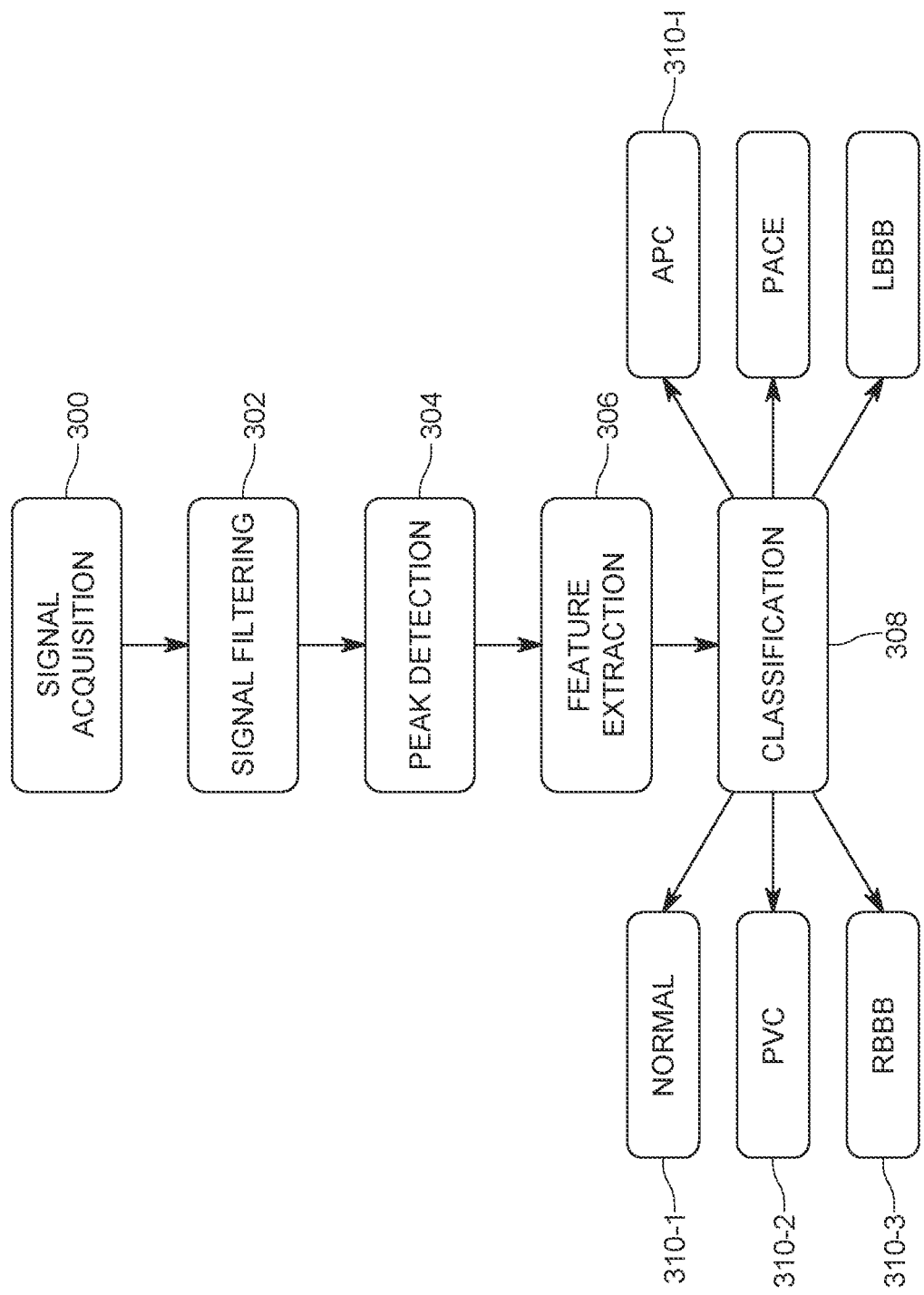
FIG. 3 is a flow chart of a method for automatically identifying a cardiovascular disease based on an ECG signal.

The cardiovascular disease diagnostic system 200 is configured to implement the functionalities discussed above according to the method illustrated in FIG. 3. The method starts in step 300 by receiving the ECG signals. If the system 200 is directly connected to the one or more electrodes 232 (in one embodiment, only three electrodes 232 are necessary for performing the method discussed herein), then the ECG signals are received directly from these electrodes. However, it is possible that system 200 receives the ECG signals over the communication unit 250, for example, if the system 200 is located away from the patient. The received ECG signals can then be stored in the memory 220 for further processing.

In step 302, the ECG signals are filtered by the ECG noise removal module 204 for removing or reducing the associated noise. In step 304 the ECG peak detection module 206 applies at least two different algorithms, as discussed later, for determining the peaks associated with the ECG signals. Based on the detected peaks, the cardiovascular diagnosis module 208 extracts in step 306 one or more features associated with the peaks of the ECG signals and in step 308, the system 200 classifies the extracted features to fit one or more cardiovascular conditions 310-1, where I is any natural number larger than 3.

Figure 4:
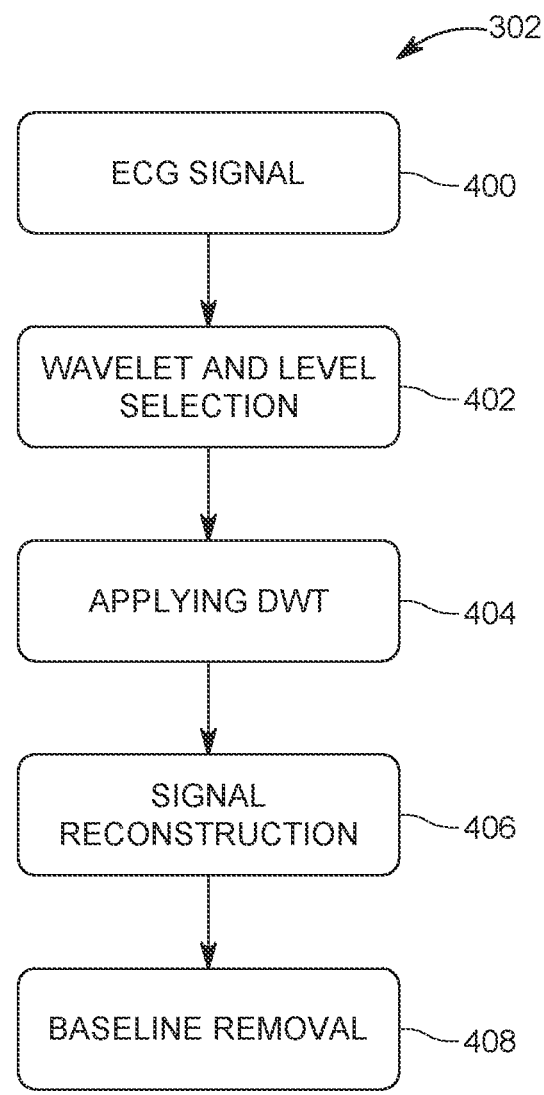
FIG. 4 is a flow chart of a method for removing artifacts from an ECG signal based on a wavelet transform.

With regard to the ECG noise removal module 204, it is known that the ECG signals are contaminated by noise and artifacts such as baseline drifts. For the accurate detection of the P, QRS, and T waves, artifacts and noise should be removed from the signal as much as possible. Thus, for the step of signal filtering 302, the baseline drift and/or the high-frequency noise are removed using a discrete wavelet transform (DWT). FIG. 4 shows the steps involved in the baseline drift removal. The ECG signal is received in step 400, and wavelet and level of decomposition selection is performed in step 402. A central frequency (Fc) is calculated to select wavelet. The Fc factor ranges from 0 to 1 depending on the similarity between the signal and the wavelet. Daubichie-4 (db4) has the highest Fc factor, and it is 0.7 for ECG signal. Next, a pseudo-frequency (Fa) is calculated at each scale using the following equation.

$$F_a = \frac{F_c}{2^a \Delta}, \qquad (1)$$

where "a" shows the scale and $\Delta$ shows the sampling period. As the baseline drift is mostly localized around 0.5 Hz, a scale with $F_a$ less than or equal to 0.5 Hz is selected similar to [7]. The selected scale in this embodiment is the scale 9. After the scale selection in step 402, the ECG signal is decomposed in step 404 into approximate and detailed coefficients using the db4. The approximate coefficients are used to extract the low-frequency components, while the detailed coefficients are used to extract the high-frequency components of the signal, similar to [8]. The low-frequency coefficients contain the baseline drift. Then, the signal is reconstructed in step 406 through an inverse discrete wavelet transform (IDWT) using only the approximate coefficients, which results in an estimation of the baseline drift. To suppress the baseline drift, the estimated baseline drift is subtracted in step 408 from the original ECG signal, which results in a baseline drift-free signal.

Figure 5A:
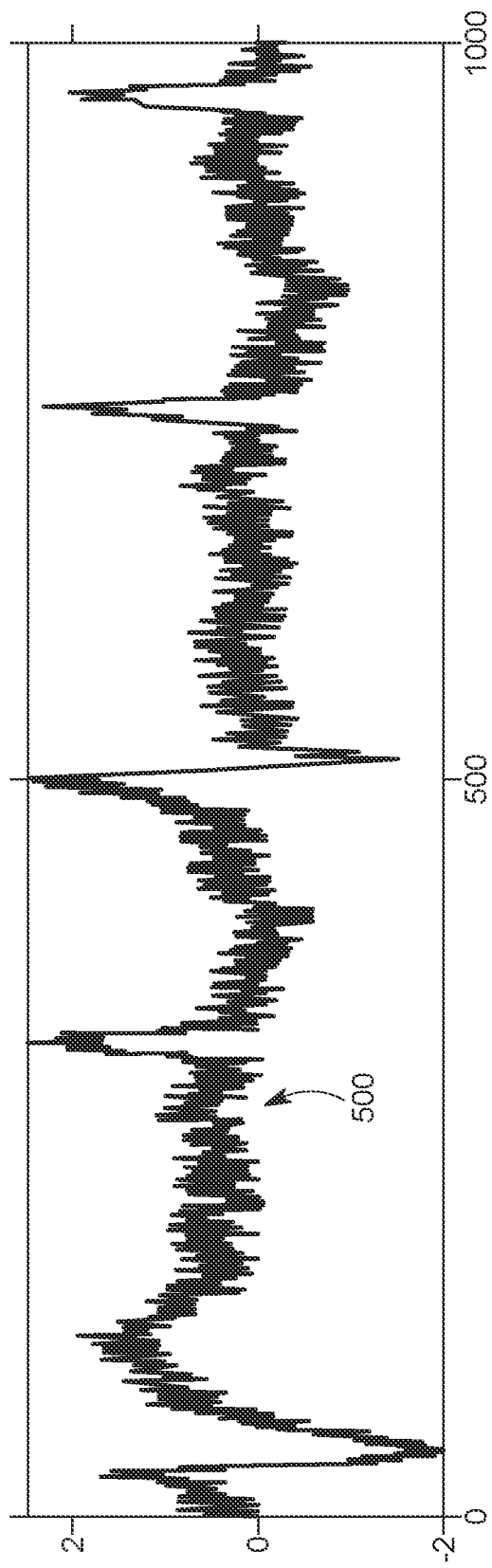
Figure 5B:
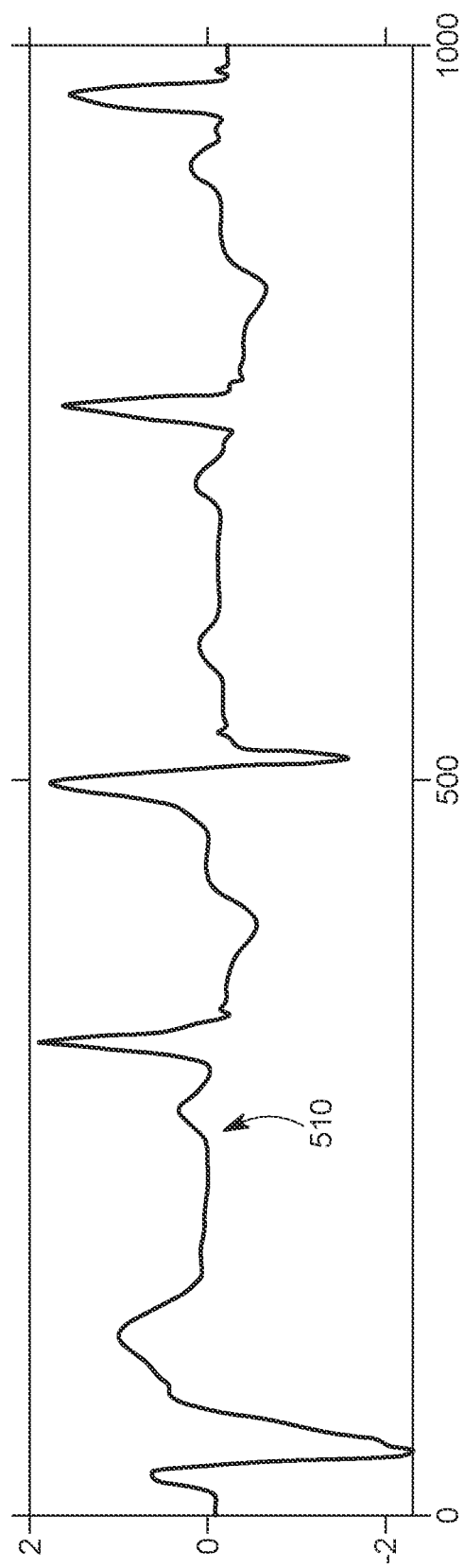
FIG. 5B illustrates the same signal after denoising.

Similarly, the high-frequency noise can be removed using the wavelet filtering. Different noises have different frequencies ranges as known from literature. After the baseline drift removal, the signal is again decomposed up to level 6 using the db4 wavelet. As most of the energy of the QRS complex is concentrated in the range of 8 to 20 Hz, the level 6 is chosen for decomposition. The QRS energy can be captured using the detailed coefficients of levels 4, 5, 6 and the approximate coefficients of level 6. The detailed coefficients of levels 1, 2 and 3 contain high-frequencies ranges from 50 Hz to 100 kHz. This noise belongs to muscle contraction noise. Therefore, the detailed coefficients are discarded and the approximate coefficients are retained at these levels. FIG. 5A shows the raw ECG signal 500 including the baseline drift and high frequency noise while FIG. 5B shows the denoised ECG signal 510 from which the baseline drift and the high-frequency noise has been removed. The denoised signal 510 is now ready for further processing for the peak detection. The signal shown in FIG. 5B is the result of the step 302.

The denoised signal 510 is now processed in step 304 for peak detection. A combination of algorithms are used in this step for the peak detection. The present embodiment discusses combining the moving averages algorithm (the first algorithm) with the FrFT (the second algorithm). The moving averages results in smoothing out the short-term events while highlighting the long-term events. Two moving averages are generated and when used together, they crossover from time to time. The use of these averages results in the detection of certain events, which are related to the P, QRS, and T waves. The implementation of the moving average is numerically efficient.

To further improve the detection performance, the FrFT is used, as now discussed. The FrFT is a generic form of a classical Fourier transform with a parameter $\alpha$ that shows its order. The FrFT of a signal can be defined as $$\text{FrFT}^\phi(t,u) = F^\phi(x(t)) = X_\phi(u) = \int_{-\infty}^{\infty} x(t) K_\phi(t,u) dt \qquad (1)$$

where $\alpha$ represents the order of the FrFT, $\phi=\alpha\pi/2$ is the angle of rotation, $F^\alpha(\cdot)$ denotes the FrFT operator, and $K_\phi(t,u)$ represents the kernel of the FrFT and is defined by:

$$K_\phi(t,u) = \qquad (2)$$

$$\left\{ \sqrt{\frac{1-j\cot\phi}{2\pi}} \exp\left(j\frac{t^2+u^2}{2}\cot\cot\phi - jtu\csc\csc\phi\right), \right.$$

for $\phi \neq n\pi$ $\delta(t-u)$, for $\phi = 2n\pi$ $\delta(t+u)$, for $\phi = 2\left(n+\frac{1}{2}\right)\pi$ where n is an integer.

Figure 6A:
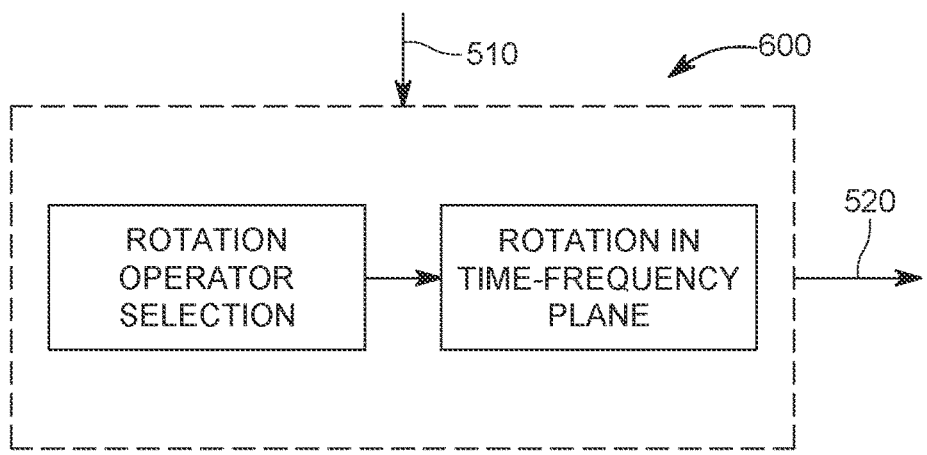
FIGS. 6A to 6C schematically illustrate the various modules used by the peak detection method.
Figure 6B:
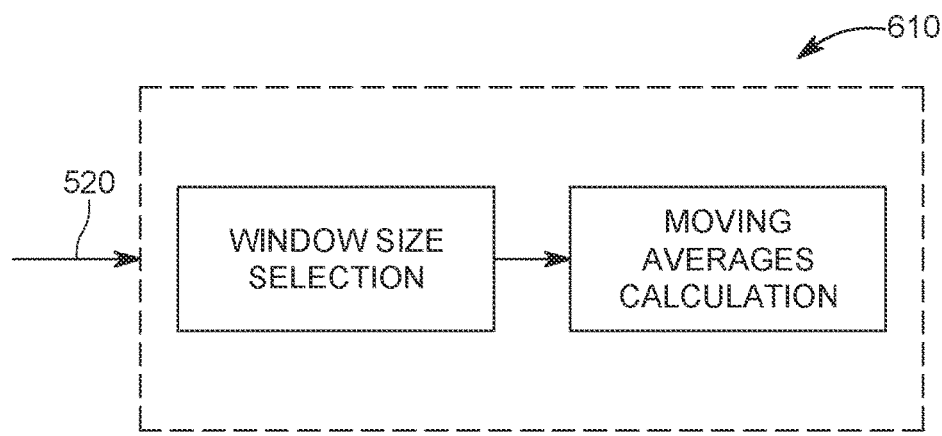
Figure 6C:
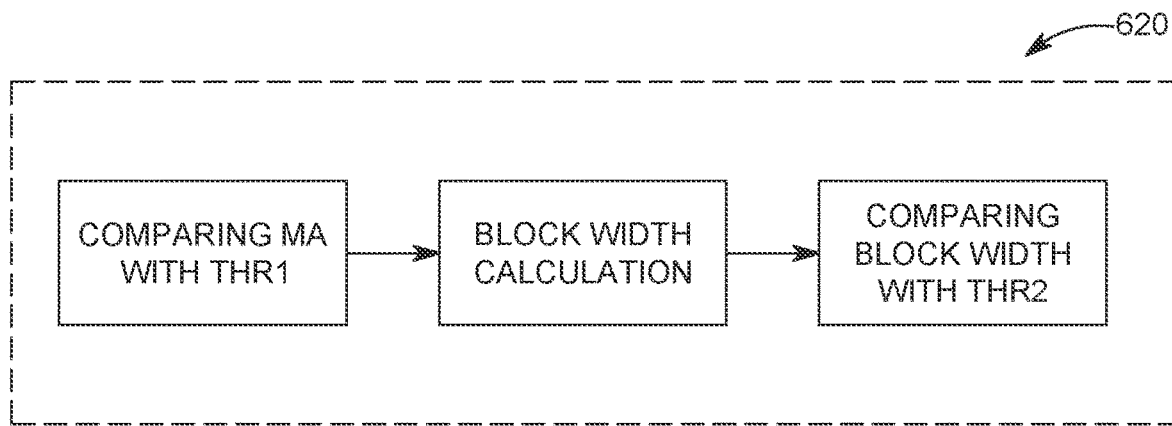

The step 304 of peak detection for the R peak is performed by passing the filtered signal 510 through different modules such as, an enhancement module 600 shown in FIG. 6A, generation of blocks of interest (BOIs) module 610 as shown in FIG. 6B, and thresholding of the BOIs module 620 as shown in FIG. 6C. More specifically, the R peaks are detected using the fusion algorithm (which is the combination of the two algorithms discussed above, i.e., FrFT and TERMA [5], [9] to [11]). The denoised signal 510 is first passed through the enhancement module 600, in which the signal is rotated in the time-frequency plane using the FrFT equation (1) using the value of $\alpha=0.2$. This value of a is chosen by try and error method to yield the best possible detection. This enhancement block is different from the simple squaring block used in the original TERMA algorithm, as the FrFT enhancement performs a much better detection. The FrFT transform includes chirp multiplication, followed by chirp convolution and again another chirp multiplication. This transformation is applied to the signal 510, which is free of the baseline drift and the high-frequency noise. The transformation rotates the signal 510 in the time-frequency plane, generating a FrFT signal 520. After applying the FrFT transform, the rotated signal 520 may be further enhanced by squaring each sample so that the large values can be boosted.

After enhancement in the module 600, the blocks of interests (BOIs) are generated in the module 610, by using the two event-related moving averages. One moving average is event-related and extracts a specific event from the rotated signal 520, while the other moving average is cycle-based and is used to extract the repeated events such as QRS complexes. A block of interest 710 is shown in FIG. 7 for the QRS wave. An event-related threshold is applied by the module 620 to the BOIs 710 to distinguish the blocks that contain the R peaks. The event-based moving averages smooth out the peaks and help to extract the area of interest. For example, the moving average MA for the even-related is defined as:

$$MA_{event}[n] = \frac{1}{W_1} \sum_{k=-l}^{l} x[n+k], \qquad (3)$$

where n is the time instant, $$l = \frac{W_1 - 1}{2},$$

while the value of the window $W_1$ depends on the duration of the event (QRS complex in this case). The time instant n is an integer and x indicates a series of points that correspond to the selected samples. The moving average for the cycle-based emphasizes the repeated cycle-based events and is defined herein as:

$$MA_{cycle}[n] = \frac{1}{W_2} \sum_{k=-p}^{p} x[n+p], \quad (4)$$

where $$p = \frac{W_2 - 1}{2}$$

while the value of the window $W_2$ depends on the duration of the heartbeat.

Figure 8:
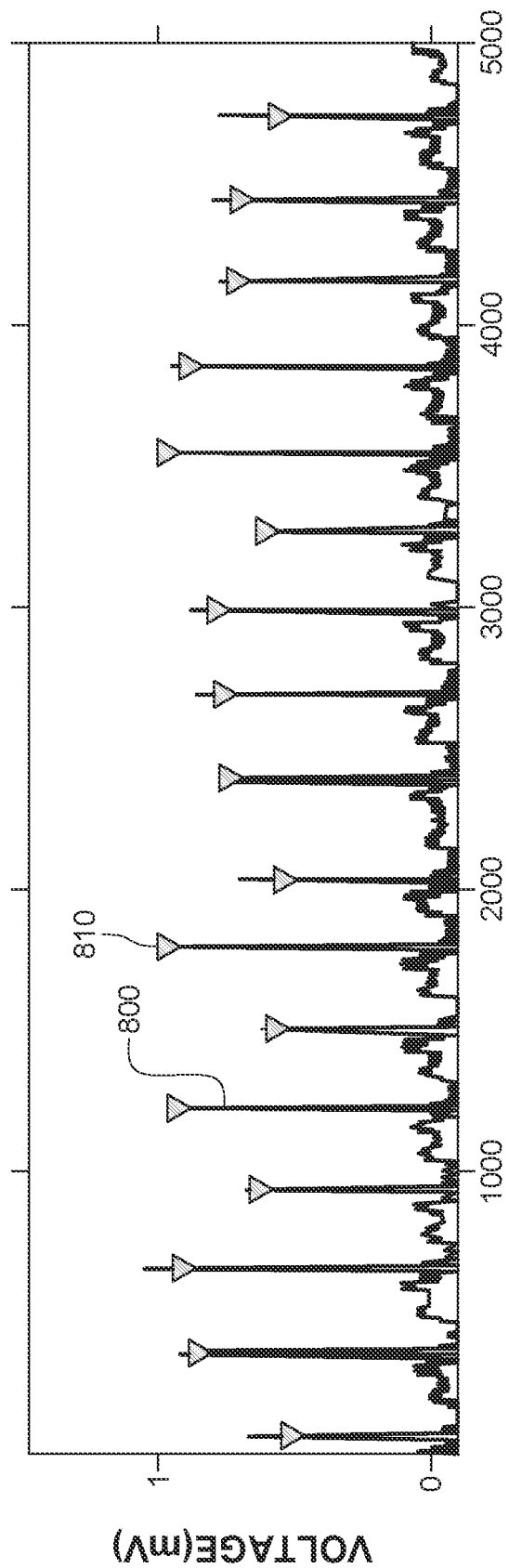
FIG. 8 shows the ECG signal and the annotated R peaks and FIG. 9 shows the detected R peaks relative to the ECG signal.
Figure 9:
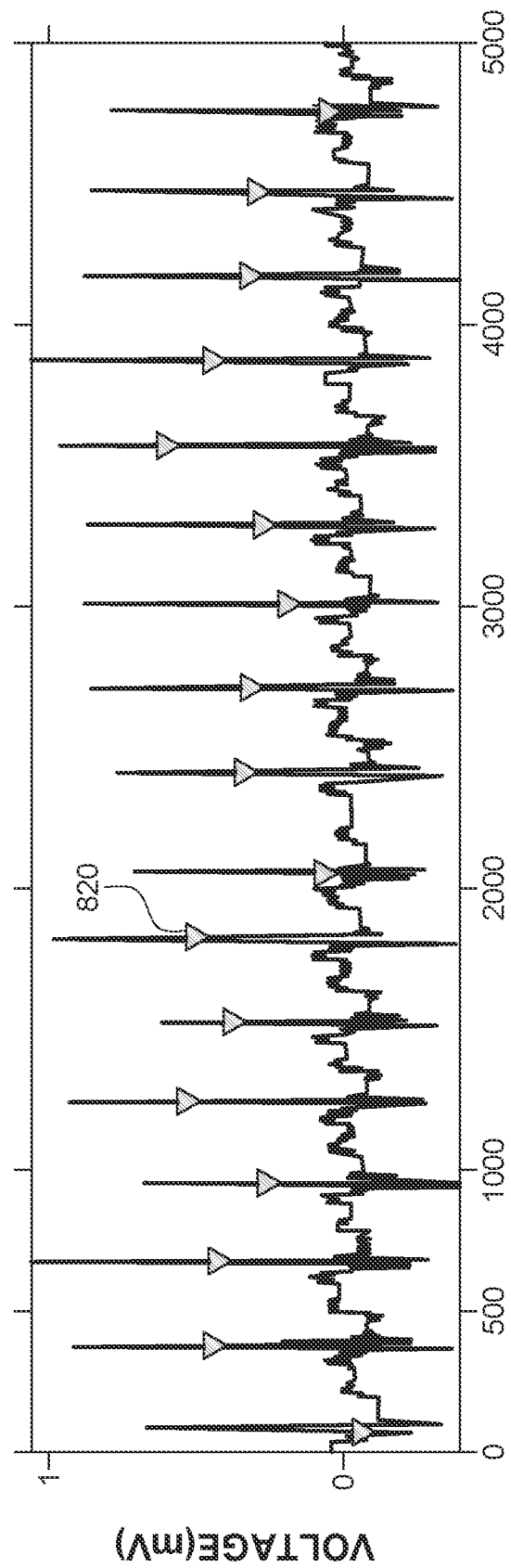

The moving averages given by equations (3) and (4) are then compared in block 620 with the selected threshold to generate the block of interests 710. If the $MA_{event}[n]$ is greater than the threshold, then the corresponding block contains the bio-signal features such as the R peaks. After generating the blocks of interests, the R peaks are detected using a search algorithm. It can be seen in FIGS. 8 and 9 that after applying the fusion algorithm (corresponding to modules 600, 610, and 620), almost all annotated R peaks 810 from the ECG signal 800 are accurately detected as detected R peaks 820.

The P and T peak detection process is now discussed. The first step is the removal of the determined R peaks from the denoised signal 510 to make the P and T peaks prominent. The R peaks are removed by setting the sample values before and after the R peak to zeros. The signal is set to zero in this embodiment in a range of 30 samples (0.083 s) before the R peak and 60 samples (0.166 s) after the R peak. For this duration, the occurring probability of the P and T waves is negligible for any CVD. Other ranges may be used. After the R peaks are removed, the signal is rotated in the time-frequency plane by applying the FrFT transform with the module 600. After applying the FrFT transform, the block of interests are generated with the module 610, by using the moving averages. The P wave duration for a normal healthy person varies within (100±20) ms and the QT interval varies within (400±40) ms. Window sizes for the moving averages are selected by module 610 depending on the normal P wave duration and the QT intervals.

The first moving average that is used to detect the P and T peaks is defined as follows:

$$MA_{peak}[n] = \frac{1}{W_3} \sum_{k=-q}^{q} x[n+q], \quad (5)$$

where $$q = \frac{W_3 - 1}{2}$$

and the value of the window $W_3$ is selected to be 55 ms and it is half the duration of the P wave. A smaller window size is chosen rather than the window size for the healthy persons, to consider the special cases of arrhythmias, which have a smaller duration. The purpose of the second moving average is to use it as a threshold for the first moving average. Thus, the second moving average is selected to be:

$$MA_{wave}[n] = \frac{1}{W_4} \sum_{k=-r}^{r} x[n+r], \quad (6)$$

where $$r = \frac{W_4 - 1}{2}.$$

Figure 10:
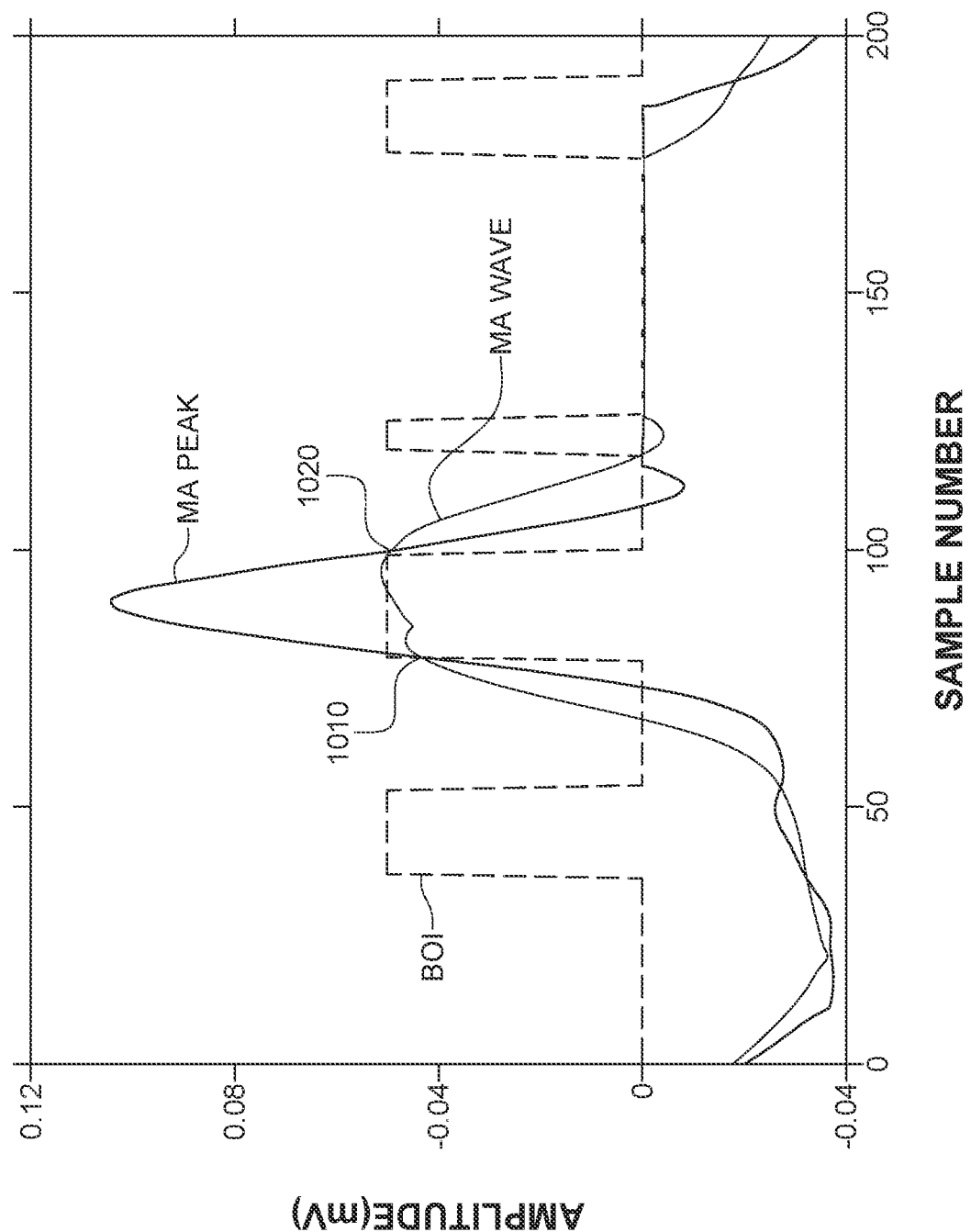
FIG. 10 shows how the block of interest for the detection of the P and T peaks are generated.

The moving averages are then passed to module 620, for applying the threshold(s) and determining the peaks. If the first moving average (given by equation (5)) is greater than the second moving average (given by equation (6)), that part of the signal is considered as BOIs, as shown in FIG. 10. FIG. 10 shows that the sequential intersection of the two moving averages, at points 1010 and 1020, define the block of interests containing the P and T peaks.

Figure 11:
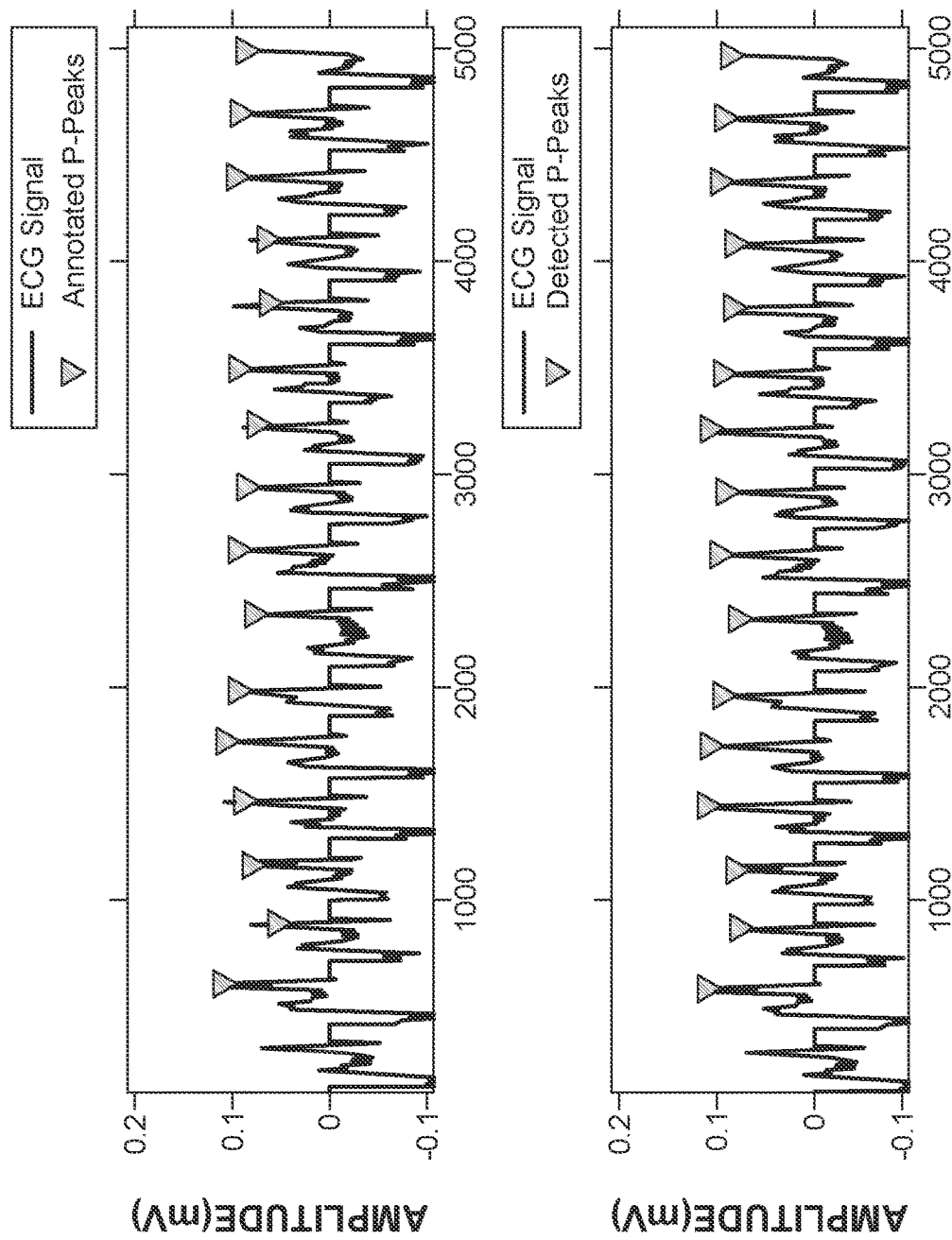
FIG. 11 illustrates the annotated and detected P peaks for an ECG signal and FIG. 12 shows the annotated and detected T peaks for the ECG signal.
Figure 12:
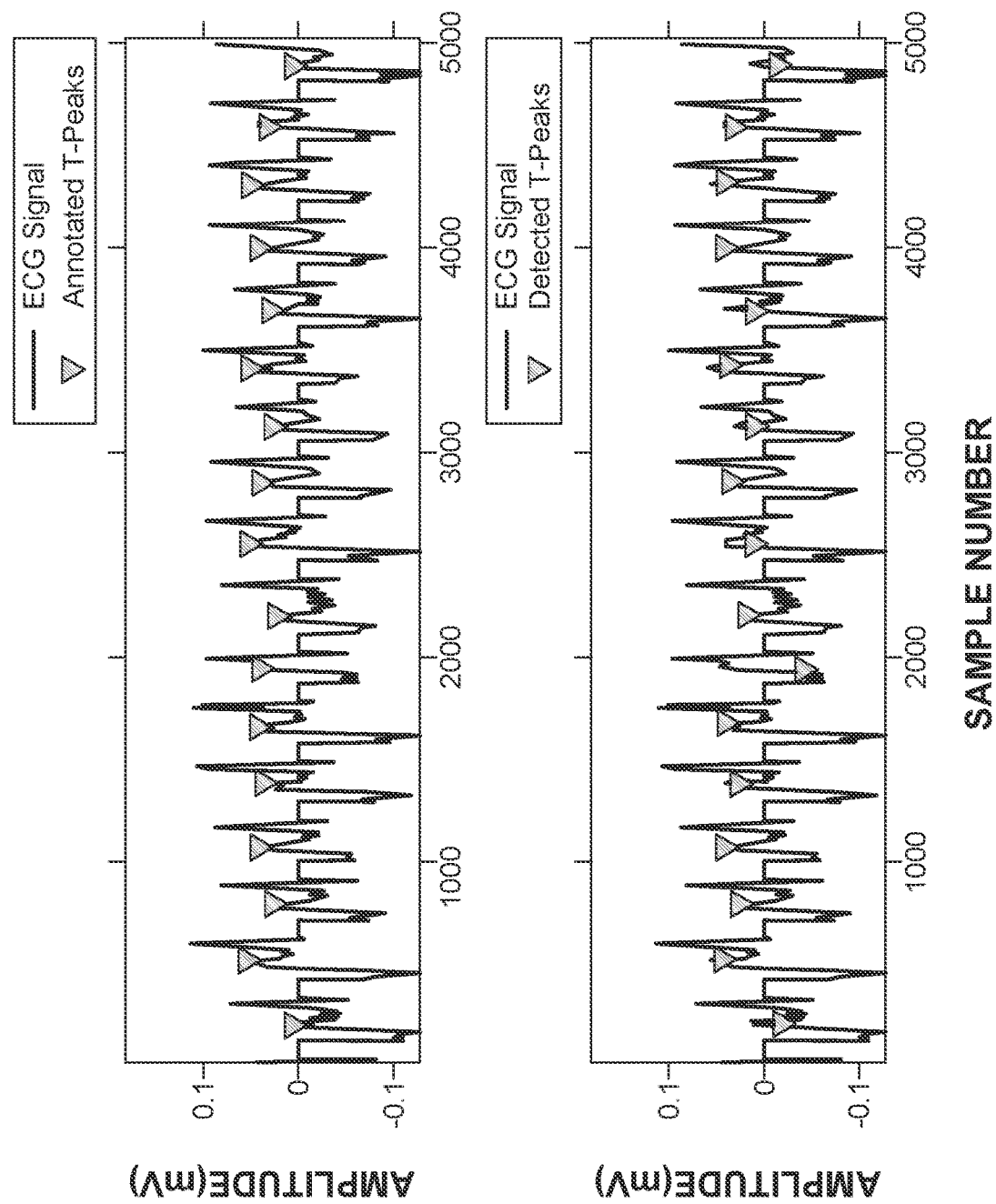

A threshold based on the PR, RR and RT intervals is applied to the two averages to distinguish the generated blocks from the blocks that contain the P and T peaks. If the distance between the maximum value of the block and the nearest R peak is within the predefined PR interval, then the maximum value of the block is referred to as the P peak. If the distance between the maximum value of the block and the nearest R peak is within the predefined RT interval, then the maximum value of the block is referred to as the T peak. FIG. 11 shows that the P peaks and FIG. 12 shows that the T peaks are accurately detected accurately after applying the fusion algorithm. The use of FrFT allows us to detect P and T wave peaks more accurately at lower computational cost.

Next, having accurately identified the various peaks of the original ECG signal, it is necessary to extract features from these peaks, and to classify the features based on a database of possible diseases associated with the peaks. To classify a heart condition, the estimation of the different peaks discussed above and shown in FIGS. 9A, 9B, 11, and 12 can be used in combination with a machine learning algorithm. Machine learning allows training on data inputs and by using statistical analysis, helps to output the values that fall within the specific range. It helps in the automatic decision-making process that is implemented in the system 200 by building different models from the sample data. However, to be able to predict which disease corresponds to the extracted peaks, the machine learning algorithm run by the system 200 needs to be trained first. Thus, to train the machine learning algorithm, in some cases, the system is provided with some inputs and predefined labels, while in other cases the inputs are unlabeled. Data training includes two steps, feature extraction and classification, which are discussed next.

With regard to the feature extraction step, different features can be extracted from the ECG signal using statistical parameters and the peak information. These features are used to classify the signal and help in disease diagnosis. In this embodiment, features are extracted from different records of the MIT-BIH arrhythmia database, Kaggle ECG Lead 2 data set PhysioNet, and 12 lead Chinese data set, all known in the art. Samples from the different records contribute towards the data set used for the feature extraction. The features considered in this embodiment include age, sex, coefficients from the AR model, coefficients from the FrFT transform, and information associated with the detected R, P and T peaks.

In one application, an Auto Regressive Model (AR) is used. The AR model of order p (AR(p) model) can be described as:

$$x(n) = \sum_{i=1}^{p} a_n x(n-i) + e(n), \quad (7)$$

where $a_1, a_2, \ldots, a_p$ represent the coefficients of the AR model, e(n) is the white Gaussian noise sample of zero mean and \sigma$^2$ variance. The AR model evaluates criteria for the selection of the model order for a sequence of AR models of successive orders, from $p_{min}$ to $p_{max}$ and computes the parameters, $a_1, \ldots, a_{opt}$. The optimum order $p_{opt}$ of an AR model is generally chosen as the optimizer of an order selection criterion. In this embodiment, the optimum order $p_{opt}$ has been chosen to have a value of 4. Thus, the fourth order AR model is used to represent the heartbeats in this embodiment. Other values may be selected for this parameter.

Next, a feature matrix is generated. The feature matrix contains the feature information of heart beats taken from the different records of the MIT-BIH arrhythmia database. Each row of the matrix shows the feature information of a single heartbeat. Each row includes different features of different heartbeats taken from the datasets. For example, if in this embodiment, four coefficients $a_1$ to $a_4$ are taken from the AR model, n coefficients are taken from the FrFT transform of the given heartbeats, and two coefficients are the PR and RT intervals, the feature vectors $\{a_1, a_2, a_3, a_4, f_1, f_2, \ldots, f_n, PR, RT\}$ for each heart beat can be concatenated together to form a feature matrix.

The PR and RT intervals are calculated as now discussed. Peak information of the P, QRS complex, and T waves has been used to extract the values of the PR and RT intervals. These intervals are important in CVDs diagnosis because many heart diseases include a change in the heart rate, removal of the P peak between two QRS complexes, an extra R peak between the P and T peaks, and so on. Any of these changes results in a change in the PR and RT intervals. These intervals also contain information of all the detected peaks and thus, these intervals have been chosen as the features to classify the different heart beats.

The classification of the ECG signal is now discussed. Classification using machine learning can help in identification of the abnormality present in the ECG signal of the patient. After identifying an abnormality in the ECG signal, the system 200 can diagnose heart diseases and thus enable the doctor to provide a better treatment to the patient. In this embodiment, the Support Vector Machine (SVM) and Multilayer Perceptron (MLP) algorithms have been used for the classification step.

The SVM is a supervised learning algorithm, which can be used for the classification and regression problems. In SVM, data is plotted in an n dimensional space where n shows the number of features. After plotting, the classification is performed by finding a hyper plane that differentiates between different classes. The hyper plane is optimized by the maximization of the margin. The hyper plane which is at higher distance from the closest data points among other hyper planes is chosen. Then, the SVM is solved based as the following quadratic problem:

$$\left( \sum_{i=1}^{n} \alpha_i - \frac{1}{2} \sum_{i,j=1}^{n} \alpha_i \alpha_j t_i t_j K(X_i, X_j) \right) \quad (8)$$

$$\text{subject to } \sum_{i,j=1}^{n} \alpha_i t_i = 0$$

$$\alpha_i \leq C, i = 1, 2, \ldots, n$$

where $\alpha \geq 0$ are Lagrange multipliers, C is a constant, and $K(X_i, X_j)$ is the kernel function. A common kernel function is the Gaussian Radial Basis function (RBF), which is defined as:

$$K(X_i, X_j) = \exp\frac{\|X_i - X_j\|^2}{2\sigma^2}. \quad (9)$$

The SVM process is very effective in higher dimensional spaces and also effective when the number of dimensions is greater than the number of samples. As compared to both the logistic regression and neural networks, the SVM sometimes gives a cleaner, and sometimes more powerful way of learning complex non-linear functions. The classification process with the SVM is divided into two steps, learning and testing. During the learning step, some features are given as an input to the SVM classifier while in the testing step, the given data set is divided into two subsets, a training data set and a testing data set. In this embodiment, the data set has been divided into training and testing subsets, with a 70% data for training and 30% for testing.

When the MLP classifier is used, an artificial neural network (ANN) algorithm is used to classify regions of interest using a methodology that performs similar functions to the human brain such as understanding, learning, solving problems and taking decisions. The ANN architecture consists of three units. The first layer is the input layer and the number of its nodes is determined by the number of the input parameters. The last layer is the output layer, and the number of its nodes is given by the desired output. The layers between the input and output layers are called the hidden layers. In this embodiment, the MLP model is a feed-forward artificial neural network. The connections between perceptrons in an MLP are forward and every perceptron is connected to all the perceptrons in the next layer, except the output layer that directly gives the result. The MLP utilizes back propagation algorithm to produce results.

To test these feature extraction algorithms, a data set from the MIT-BIH arrhythmia data base has been used. The system 200 was validated over all the 48 records of the database. After preprocessing, the P, R and T peaks were detected for each record. After peak detection, different features were extracted from the signal for the classification. The extracted features were passed to the SVM classifier to classify the data set. The data set was classified into normal beat (Normal), premature ventricular construction (PVC), atrial premature contraction (APC), left bundle branch block beat (LBBB), right bundle branch block beat (RBBB), and paced beat (Pace) heart beats. 70% of the data was chosen as training while 30% was chosen as testing data. Different features were also extracted from the Kaggle ECG 2 lead data set and 12 lead Chinese data set. The MLP model was trained on the MIT-BIH data set and tested over the same databases. Normal, RBBB and PVC beats are classified using these data sets. The performance of the proposed algorithm is tested by using different metrices. Several metrices are used to determine the performance of the algorithms run on the system 200, such as overall accuracy, sensitivity (precision), positive predictivity (recall), f1-Score, and Error rate. These metrices are defined as:

$$\text{Overall Accuracy} = \frac{TP+TN}{TP+TN+FP+FN}$$

$$\text{Sensitivity } (SE) = \frac{TP}{TP+FN}$$

$$\text{Positive}-\text{Predictivity } (+Pr) = \frac{TP}{TP+FP}$$

$$f_1 - \text{score} = 2\frac{\text{precision} * \text{recall}}{\text{precision} + \text{recall}} = \frac{TP}{TP+\frac{1}{2}(FP+FN)}$$

$$\text{Error Rate } (Err) = \frac{FP+FN}{TP}$$

where FN represents the false-negative defined as the annotated peaks not detected by the algorithm, FP represents the false-positive defined as peaks which are detected but are not actually present and if the peak is detected within the 30 ms interval of the annotated peaks, it is defined as TP. To assess the performance of the algorithm, the FN and TP are estimated.

With regard to the detection step, the table in FIG. 13 illustrates the performance of the fusion algorithm as compared to the TERMA algorithm. The fusion algorithm has been tested over all the 48 records of the MIT-BIH arrhythmia database. The table in FIG. 14A shows the performance of the algorithm for the detection of P and T peaks over the first 10 records of the MIT-BIH arrhythmia database while the table in FIG. 14B shows the same performance, but over the remaining 38 records of the MIT-BIH arrhythmia database. The inventors found an improvement in the Error Rate and Sensitivity of the fusion algorithm over the TERMA algorithm. For the P peaks detection, the fusion algorithm results in SE of 75.8% and Err of 0.40 as compared to SE of 67.5% and Err of 0.51 in the case of TERMA. For the T peaks detection, the fusion algorithm results in SE of 59.2% and Err of 1.04 as compared to SE of 42.8% and Err of 1.15 in the case of TERMA.

With regard to the classification step, after the peak detection, the data set is classified by passing the extracted features through the SVM classifier. In this embodiment, the Scikit-learn (a machine learning algorithm implemented in Python) has been used for machine learning model building. The records 100m, 109m, 118m, 107m, 208m and 232m from the MIT-BIH arrhythmia database were used for the feature extraction and classification. In this embodiment, a total of 36 features were extracted, which contains 32 features from the DWT transform and 4 features from the AR model. The total number of beats extracted from the Normal, LBBB, RBBB, PACE, PVC and APC records were 2,237, 2,490, 2,165, 2,077, 992 and 1,382 respectively. The total number of data used in training was equal to 7,940 beats. Another 3,403 data points have been left for testing. Under these conditions, the SVM algorithm gives an overall accuracy of 99.68%. In addition, the algorithm was tested by extending the data set to other records of MIT-BIH data base.

To obtain the optimal SVM classification, two parameters C and $$\gamma = \frac{1}{2\sigma^2}$$

should be adjusted. In this embodiment, the parameter C has been selected to be 65,536 and $\gamma=2.44e^{-4}$. The Normal, PVC, APC, LBBB, RBBB and PACE heart beats have been extracted from different records of the MIT-BIH database. The feature matrix was generated using 6 different features for the samples of each extracted heartbeat. The feature extraction work has been extended by combining different sets of features as shown in the table of FIG. 15. The SVM classifier was tested for two different types of data. One data contains the information from the annotations (which is available online) while the other data contains the peak information from the detected peaks. The SVM classifier shows an overall accuracy of 96.6% using annotations and 93.9% without annotations.

The MLP classifier was also tested. In this embodiment, the same data set has also been used for the classification process. The features were extracted and passed through the classifier. This classifier shows an overall accuracy of 99.79% for the same set of 36 features shown in the first row in the table in FIG. 15. The table in FIG. 16 shows the performance comparison of the classifiers SVM and MLP in terms of precision, recall, and f1-Score.

The classifiers discussed above have also been training and testing on the 12 Lead ECG SPH Data set. The data set consists of four parts, ECG raw Data, ECG denoised data, diagnosis file, and attributes file. For each subject, the data file includes headers which represents the ECG lead. This database contains 12-lead ECGs of 10,646 patients with 500 Hz sampling rate that features 11 common rhythms and 67 additional cardiovascular conditions. The data has been labelled by professional experts. For each subject, the signal is 10 sec long, which contains 5,000 samples for each lead. Data for each patient is of 5,000×12 dimensions.

For this data-set, 11 rhythms are merged into 4 groups (SB, AFIB, GSVT, SR). SB only includes sinus bradycardia, AFIB consists of atrial fibrillation and atrial flutter (AF), GSVT contains supra ventricular tachycardia, atrial tachycardia, atrio-ventricular node reentrant tachycardia, atrio-ventricular reentrant tachycardia and sinus atrium to atrial wandering rhythm, and SR includes sinus rhythm and sinus irregularity. AFIB or AF are classified into AFIB group. Sinus rhythm and sinus irregularity are merged into the SR group, so that it can be distinguished from the GSVT group. Sinus irregularity can be distinguished from sinus rhythm by one simple criteria of PR interval variability. After regrouping these data signals, a set of features has been extracted. A total of 100 records, 25 from each group, are selected from the database. A total of 16 features are extracted, with 4 features being taken from the coefficients of the AR model.

To apply the AR model, a segment from each data set is selected. For this purpose, the R peaks are detected using the fusion algorithm discussed above with regard to FIGS. 6A to 6C. After detection, one segment from each signal is selected in such a way that it contains 300 samples, 90 samples before the R peak and 210 samples after the R peak. The AR model is applied on the set of these 300 samples and its coefficients are calculated. 12 other features such as age, gender, ventricular rate, atrial rate, QRS duration, QT interval, QRS count, RAxis, TAxis, QOnset, QOffset, and TOffset are taken from the diagnosis file present in the data set. This data set is trained and tested using the SVM and MLP classifiers. The MLP classifier has shown an overall higher accuracy of 95%, as illustrated in table of FIG. 17. When the MLP classifier has been trained and tested with data sets from other sources, e.g., the St Petersburg INCART 12-lead arrhythmia database and the 12-lead Chinese database to classify the Normal, RBBB and PVC beats, the classifier has shown an overall accuracy of 93.6% for INCART and 65% for the Chinese database.

The above discussed embodiments rely on the fusion algorithm, which is based on a combination of wavelets, FrFT transform, and TERMA averages to detect the R, P, and T peaks. The wavelets were used to denoise the signal, while the FrFT and TERMA were used for the accurate detection of the peaks. After peak detection, the results were used for the classification of the ECG signals using different classifiers such as the SVM and MLP. Different numbers of features are extracted from two different data-sets and passed through the classifiers. Heart beats are also classified using two different data sets for training and testing. The fusion algorithm when used with these classifiers has shown a very high overall accuracy regarding the classification of the different heart beats.

Figure 2:
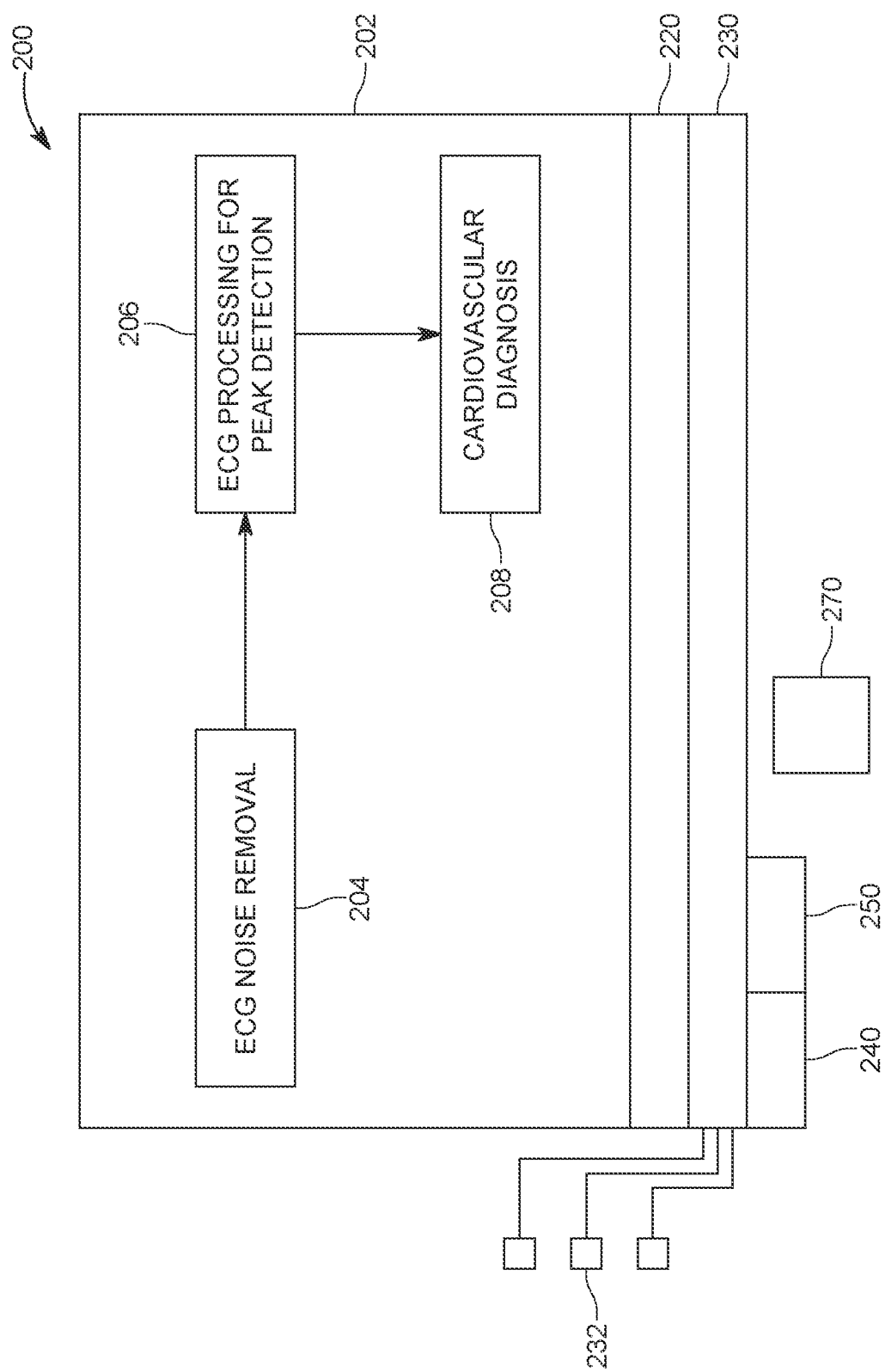
FIG. 2 is a schematic diagram of an autonomous and independent cardiovascular disease diagnostic system.
Figure 18:
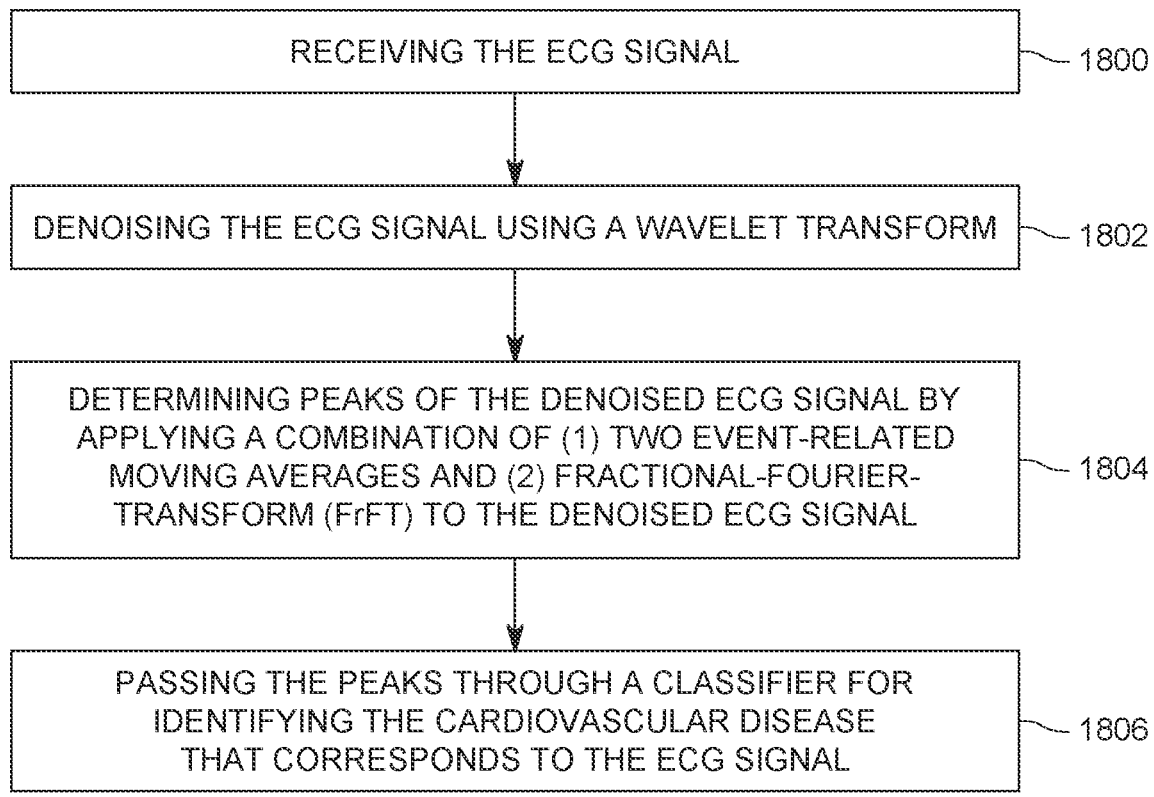
FIG. 18 is a flowchart of a method for automatically and independently associating a cardiovascular disease with an ECG signal.

The algorithms discussed above can be implemented as an autonomous and independent cardiovascular diagnostic method into the system 200 shown in FIG. 2. Such a method includes, as illustrated in FIG. 18, a step 1800 of receiving the ECG signal, a step 1802 of denoising the ECG signal using a wavelet transform, a step 1804 of determining peaks of the denoised ECG signal by applying a combination of (1) two event-related moving averages and (2) fractional-Fourier-transform (FrFT) to the denoised ECG signal, and a step 1806 of passing the peaks through a classifier for identifying the cardiovascular disease that corresponds to the ECG signal. The two event-related moving averages calculate a first average that is related to an event on the ECG signal, and a second average that is cycle-based and is related to repeated events on the ECG signal. The method may further include generating a block of interest based on the two even-related moving averages. The block of interest is defined by two adjacent interactions of the first average and the second average when plotted against a sample number. The method may further include determining first R peaks of the ECG signal, and determining second P and T peaks of the ECG signal. The R peaks are removed from the ECG signal before determining the P and T peaks.

The step of passing may include applying an auto regressive model to the peaks associated with the denoising ECG signal to extract features. The features include one or more of coefficients of the auto regressive model, coefficients of the FrFT transform, and various peak intervals associated with the ECG signal. The peak intervals are calculated based on the determined peaks. In one application, the features include four coefficients of the auto regressive model, n coefficients of the FrFT transform, and two PR and RT peak intervals associated with the ECG signal, where n is an integer larger than 2. The classifier can be a support vector machine classifier that uses a Gaussian radial basis function as a kernel function.

The disclosed embodiments provide a cardiovascular disease diagnostic system and method that autonomously and independently associates a cardiovascular disease with received ECG signals, based on a fusion algorithm for detecting the peaks of the ECG signals, and a classifier for mapping the peaks to the cardiovascular disease. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

[1] O. Adeluyi and J. A. Lee, "R-reader: A lightweight algorithm for rapid detection of ecg signal r-peaks," in 2011 2nd International Conference on Engineering and Industries (ICEI). IEEE, 2011, pp. 1-5.

[2] R. Mabrouki, B. Khaddoumi, and M. Sayadi, "R peak detection in electrocardiogram signal based on a combination between empirical mode decomposition and hilbert transform," in 2014 1st International Conference on Advanced Technologies for Signal and Image Processing (ATSIP). IEEE, 2014, pp. 183-187.

[3] M. Elgendi, M. Jonkman, and F. De Boer, "R wave detection using coiflets wavelets," in 2009 IEEE 35th Annual Northeast Bioengineering Conference. IEEE, 2009, pp. 1-2.

[4] M. Elgendi, "Fast qrs detection with an optimized knowledge-based method: Evaluation on 11 standard ecg databases," PloS one, vol. 8, no. 9, pp. e73557, 2013.

[5] M. Elgendi, "Terma framework for biomedical signal analysis: An economic-inspired approach," Biosensors, vol. 6, no. 4, pp. 55, 2016.

[6] M. Elgendi, M. Meo, and D. Abbott, "A proof-of-concept study: Simple and effective detection of p and t waves in arrhythmic ecg signals," Bioengineering, vol. 3, no. 4, pp. 26, 2016.

[7] G. Vega-Martinez, C. Alvarado-Serrano, and L. Leija-Salas, "Ecg baseline drift removal using discrete wavelet transform," in 2011 8th International Conference on Electrical Engineering, Computing Science and Automatic Control. IEEE, 2011, pp. 1-5.

[8] P. Karthikeyan, M. Murugappan, and S. Yaacob, "Ecg signal denoising using wavelet thresholding techniques in human stress assessment," International Journal on Electrical Engineering and Informatics, vol. 4, no. 2, pp. 306, 2012.

[9] S. R. Subramaniam, B. W. K. Ling, and A. Georgakis, "Motion artifact suppression in the ecg signal by successive modifications in frequency and time," in 2013 35th Annual International Conference of the IEEE Engineering in Medicine and Biology Society (EMBC). IEEE, 2013, pp. 425-428.

[10] H. M. Ozaktas, O. Arikan, M. A. Kutay, and G. Bozdagt, "Digital computation of the fractional fourier transform," IEEE Transactions on signal processing, vol. 44, no. 9, pp. 2141-2150, 1996.

[11] T. Yaqoob, S. Aziz, S. Ahmed, O. Amin, and M. S. Alouini, "Fractional fourier transform based qrs complex detection in ecg signal," in ICASSP 2020-2020 IEEE International Conference on Acoustics, Speech and Signal Processing (ICASSP). IEEE, 2020, pp. 931-935.

What is claimed is:

1. A system for automatically and independently associating a cardiovascular disease with an electrocardiogram, ECG, signal, the system comprising:
   an interface for receiving the ECG signal; and
   a logic circuit connected to the interface and configured to:
   denoise the ECG signal using a wavelet transform;
   determine peaks of the denoised ECG signal by applying a combination of (1) two event-related moving averages and (2) fractional-Fourier-transform (FrFT) to the denoised ECG signal; and
   pass the peaks through a classifier for identifying the cardiovascular disease that corresponds to the ECG signal.

2. The system of claim 1, wherein the two event-related moving averages calculate a first average that is related to a single event on the ECG signal, and a second average that is cycle-based and is related to repeated events on the ECG signal.

3. The system of claim 2, wherein the logic circuit is further configured to:
   generate a block of interest based on the two event-related moving averages.

4. The system of claim 3, wherein the block of interest is defined by two adjacent crossings of the first average and the second average when plotted against a sample number.

5. The system of claim 4, wherein the logic circuit is further configured to:
   determine first R peaks of the ECG signal; and
   determine second P and T peaks of the ECG signal,
   wherein the R peaks are removed from the ECG signal before determining the P and T peaks.

6. The system of claim 1, wherein the logic circuit is further configured to:
   apply an auto regressive model to the peaks associated with the denoised ECG signal to extract features.

7. The system of claim 6, wherein the features includes one or more of coefficients of the auto regressive model, coefficients of the FrFT transform, and various peak intervals associated with the ECG signal.

8. The system of claim 6, wherein the features include four coefficients of the auto regressive model, n coefficients of the FrFT transform, and two PR and RT peak intervals associated with the ECG signal, where n is an integer larger than 2.

9. The system of claim 7, wherein the peak intervals are calculated based on the determined peaks.

10. A non-transitory computer readable medium including computer executable instructions, wherein the instructions, when executed by a computer, implement a method for automatically and independently associating a cardiovascular disease with an electrocardiogram, ECG, signal, the method comprising:
    receiving the ECG signal;
    denoising the ECG signal using a wavelet transform;
    determining peaks of the denoised ECG signal by applying a combination of (1) two event-related moving averages and (2) fractional-Fourier-transform (FrFT) to the denoised ECG signal; and
    passing the peaks through a classifier for identifying the cardiovascular disease that corresponds to the ECG signal.

* * * * *